United States Patent [19]

Ghosh et al.

[11] Patent Number: 5,431,924

[45] Date of Patent: Jul. 11, 1995

[54] ANTI-INFLAMMATORY COMPOSITION DERIVED FROM EMU OIL

[75] Inventors: Peter Ghosh, Fairlight; Michael Whitehouse, Millswood; Michael Dawson, Newton; Athol G. Turner, Forestville, all of Australia

[73] Assignee: Emu Products Western Australia Pty. Ltd., Claremont, Australia

[21] Appl. No.: 50,423

[22] PCT Filed: Nov. 14, 1991

[86] PCT No.: PCT/AU91/00517

§ 371 Date: Jul. 16, 1993

§ 102(e) Date: Jul. 16, 1993

[87] PCT Pub. No.: WO92/08470

PCT Pub. Date: May 29, 1992

[30] Foreign Application Priority Data

Nov. 14, 1990 [AU] Australia ............................ PK3363

[51] Int. Cl.6 ............................................. A61K 47/00
[52] U.S. Cl. ..................................... 424/522; 514/825
[58] Field of Search ........................... 424/522; 514/825

[56] References Cited

PUBLICATIONS

Pat. Abst of Japan C-20 p. 21 JP.A, 55-66514 (Sakurama)-May 5, 1988.

J. F. Blair "South Westerners Grow Emu, & Then Exotic Animals "Feedstuffs Jan. 28, 1990, p. 31.

O'Brien, et al., Proc. Aust. Soc Animal Prod. 18: 101-111, 1990.

Bennett, George, "Observations Pricipally on the Animal and Vegetable Productions of New South Wales, New Zealand," *Gatherings of a Naturalist in Australasia,* published London: John Van Voorst, Paternoster Row, pp. 216-219 (1860).

Leichhardt, L., "Journals, Lost and Found," *Journal of an Overland Expedition in Australia,* published London: T. W. Boone, pp. 388-389 (1847).

Naughton, Joan M., et al., "Animal Foods in Traditional Australian Aboriginal Diets: Polyunsaturated and Low in Fat," *Lipids* 21(11):684-690 (1986).

"Notes on the Field Sports and Fauna of Australia Felix," *Bush Wanderings of a Naturalist,* by an Old Bushman, published London: Routledge, Warne & Routledge (1861).

"Emu oil called a miracle," *Sun* p. 7 (Apr. 16, 1990).

*Primary Examiner*—John W. Rollins
*Attorney, Agent, or Firm*—Patrea L. Pabst

[57] ABSTRACT

A biologically active component of emu oil is disclosed which is useful in pharmaceutical composition for the treatment of inflammation of environmental and systemic origins. Pharmaceutical composition including emu oil and dermal transport enhancing compounds are also disclosed as useful topical anti-inflammatory treatments.

17 Claims, 1 Drawing Sheet

Inhibition of human granulocyte elastase by EMU OIL preparations (H.G.E. 50 ng).

- ● — EMU OIL (Acetone fractionated
- ○ — EMU OIL (Batch 67)
- ■ — EMU OIL (Batch 181)

ANTI-INFLAMMATORY COMPOSITION DERIVED FROM EMU OIL

FIELD OF THE INVENTION

This invention relates to compositions for topical application that are useful for the treatment of musculoskeletal and dermatological conditions, in particular to composition based on emu oil and compounds that act to provide for its effective transdermal transport.

The invention further relates to methods for the treatment of the aforementioned conditions using these compositions.

The invention still further relates to compounds derived from emu oil which have anti-inflammatory properties.

For the purposes of this specification, the term "emu oil" refers to oils and preparations of oils derived from the emu (Dromais Novae—Hollandiae).

BACKGROUND ART

Within recent years there has been considerable interest in the role of the ingestion of polyunsaturated fatty acids in the prevention or treatment of arthritis, soft tissue inflammation and cardiovascular disease. This interest has arisen from the observation that Greenland Eskimos, on a traditional native diet, showed disease patterns quite different from age-matched individuals in Europe and North America. The most striking differences observed were the reduced incidence of heart disease, asthma, psoriasis and rheumatoid arthritis in Eskimo populations (1).

Examination of the Eskimo dietary lipid intake showed elevated levels of highly unsaturated fatty acids (HUFAs) arising from their high consumption of fish and marine, mammals. Subsequent clinical trials initiated by Kremer and co-workers (2) have demonstrated that the manipulation of the dietary intake of fatty acids to include higher levels of HUFAs in caucasian patients with rheumatoid arthritis could decrease the symptoms of arthritis.

The mechanism of action of this dietary intervention was considered, in part, to be dependent on the ability of the HUFAs to act as competitive substrates for enzymes involved in prostaglandin and leukotriene biosynthesis. Eicosapentaenoic acid (EPA) (20:5, n=3) and docosahexaenoic acid (22:6, n=3) are the principle long chain unsaturated fatty acid triglycerides in fish oil. EPA incorporated into cell membranes may be converted via the cyclooxygenase enzymes into the regulant prostaglandins, thromboxanes and prostacyclins of the 3-series (2-5) whereas $PGE_2$ produced from arachidonic acid precursors was a potent mediator of inflammation. EPA metabolised via the lipoxygenase pathway produces leukotriene B5 (2-5). Leukotriene B5 is 10-30 times less potent an inflammogen than leukotriene B4 which is normally produced from arachidonic acid. Thus dietary fish oil supplementation may support endogenous anti-inflammatory activity by modifying the production of harmful mediators within the animal's tissues.

An alternative pathway of unsaturated fatty acid metabolism is via the C18-triunsaturated fatty acids, gamma and alpha linolenic acid. While the alpha isomer (9, 12, 15 octadecatrienoic acid) may be shunted into the prostaglandin $E_3$ pathway, gamma linolenic acid (6, 9, 12 octadecatrienoic acid) is converted into dihomo-gamma-linolenic acid (DGLA) which is the biosynthetic precursor of the the anti-inflammatory prostaglandin $E_1$ ($PGE_1$) (6).

Evening primrose oil is also a rich source of gamma linolenic acid (7) and has been demonstrated to suppress chronic adjuvant induced polyarthritis in the rat (6) as well as in patients with rheumatoid arthritis (8).

There have been limited studies on the effects of administering these C18 unsaturated fatty acids topically for the treatment of inflammatory conditions.

In PCT/AU89/00555 (WO 90/07331) it is disclosed that linseed oil and other plant derived oils, which contain alpha linolenic acid, when dispersed in an appropriate solvent or thinner display topical anti-inflammatory activity. The specification goes on to disclose that the activity of this composition is thought to arise due to its alpha linolenic acid (9, 15, 15, octadecatrienoic acid) content. Suitable thinners, which in the context of the application mean compounds for increasing the transdermal transport of linseed oil, are said to be mineral or distilled turpentine, methyl,ethyl- and isopropylsalicylate esters, eucalyptol (cineole) tea tree oil and oil of wintergreen. These thinners in combination with the linseed oil are stated to exhibit synergism and a surprising anti-inflammatory effect.

DISCLOSURE OF THE INVENTION

Figure 1:
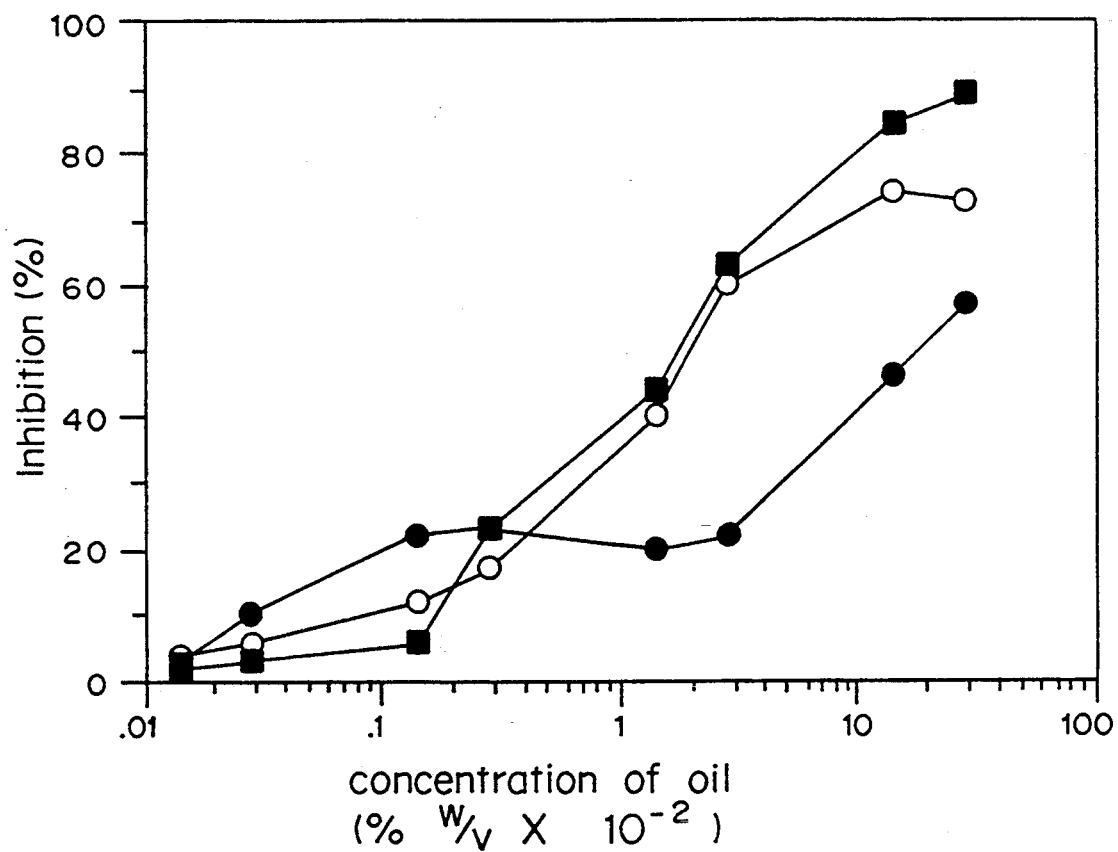
FIG. 1 is a graph showing the inhibition of human granulocyte elastase by EMU OIL preparations (H.G.E. 50 ng). The percent inhibition is compared to the concentration of oil (% weight/volume X $10^{-2}$). The darkened circles represent EMU OIL (acetone fractionated). The open circles represent EMU OIL (Batch 67). The darkened squares represent EMU OIL (Batch 181).

The present inventors in their investigation of emu oil sought to determine if this animal oil had any anti-inflammatory, anti-proteolytic or sun protective activity.

Oils extracted or rendered from emu body fats are known to contain triglyceride esters of long chain fatty acids including oleic acid and linoleic acid as well as the saturated fatty acids, palmitic and stearic (9).

It was found that whilst potent anti-proteolytic activity could be demonstrated for emu oil against purified human granulocyte elastase using appropriate in vitro assays, as shown in FIG. 1, when the oil was applied topically to the dorsal skin of rats in which a polyarthritis was induced by the injection into the tail base of a mixture of M.tuberculosis (500 ug) and squalene (500 uL), there was no reduction in the inflammatory reaction, as determined by a decrease in the swelling (oedema) of the animal's paws. On the other hand, if to the emu oil was added a miscible diluent such as isopropyl alcohol, amyl alcohol or acetate, ethyl, methyl or isopropylsalicylate, tea tree oil, eucalyptus oil, cineole or the like and the mixture applied to the skin of the rats, potent anti-inflammatory activity was observed, as is shown in Tables 1-4 and 7-10.

However, when the anti-inflammatory emu oil batches used in these experiments were analysed by GLC and GLC-mass spectroscopy using purified fatty acids of known structures as standards (Tables 5 and 6) it was found that apart from three batches (157, 203 and 988) none of the oils contained detectable levels of gamma or alpha linolenic acid. This was somewhat surprising in view of the disclosure of WO90/07331.

This finding led to the conclusion that the observed anti-inflammatory activity of emu oils, when combined with a diluent which improved transdermal absorption, was unrelated to the polyunsaturated fatty acid content of the emu oil.

This hypothesis was tested by examining various plant oils known to be rich in gamma and alpha linolenic acid in the same animal arthritis model as used for the emu oil experiments. The results of these experiments are shown in Tables 1–4 and are summarised in Table 7 which shows the unsaturated fatty acid content of the oils and an index of anti-inflammatory activity of all preparations side by side.

As can be seen from Table 7, some plant oils rich in gamma and alpha linolenic acid were found to be less active than the emu oils which were devoid of linolenic acid when they were examined under the same conditions. This is exemplified by the results obtained for emu oil batch 135, evening primrose oil and rape seed oil when each was admixed with ethylsalicylate as a diluent. It is also evident the presence of linoleic acid or oleic acid triglycerides in the oil appeared not to be related to the biological activity of the oils since safflower oil and olive oil (both known to be particularly rich in these two components) (9) were far less active than all batches of emu oil examined when these were diluted with cineole for example. Furthermore, a comparison of the emu oil with oil derived from free range chicken fat using cineole as the diluent showed a lack of anti-inflammatory activity of the latter (Table 3) even though the polyunsaturated fatty acid content of the chicken oil was higher than that of emu oil (Table 6).

Of course while it is known (9) and confirmed here (Tables 6 and 7) that the emu oil is predominantly composed of triglyceride esters of saturated and the unsaturated fatty acids these are not the only components present. Mammalian fats are well known to provide a depot for other naturally occurring lipophilic compounds. These compounds would include the fat soluble vitamins such as vitamin A, D and E as well as their precursors and metabolites. An important property of these compounds is their ability to act as antioxidants particularly for oxygen derived free radicals which are involved in the biosynthesis of prostaglandins and leukotrienes (3, 4, 5).

The carotenoids are yellow pigments which occur in plants and are known to accumulate in fats. These too may provide antioxidant activity. Similarly, bile pigments including bilirubins and haemoglobin breakdown products may also provide the requisite antioxidant activity. In addition, other compounds may be ingested by the animal through their diet and these, together with their metabolites, may deposit in the fat storage depots.

The natural diet of the emu consists of seeds, berries, grasses, leaves and plants present within the Australian bush which would be expected to contain a large variety of carotenoids, vitamins, terpenes, saponagens, flavones and other naturally occurring bioactive occurring compounds. It is believed by the inventors, without being bound to theory, that it is the further presence of such substances within emu oil which confer upon it the potent anti-inflammatory activity observed. While it is clear that this activity can only become manifest when a suitable vehicle is used to transport these components through the skin and into the blood stream of the animal, it remains to be demonstrated that the unsaturated fatty acids present are also so transported. Nevertheless, even if these triglycerides are not absorbed and remain associated with the skin, the potent anti-elastase activity demonstrated to be present in the emu oil (FIG. 1), which probably arises from its high oleic acid content (11, 12) could provide a local anti-inflammatory as well as antidegenerative effect to dermal tissues. This could be particularly relevant during dermal inflammation where cell and tissue damage produced by exposure to strong UV radiation, as in sunburn, occurs. In these cases it is known that tissue components such as elastin (13), proteoglycans (14) and collagen (15) are degraded or modified by elastase-like proteinase released by the dermal or invading inflammatory cells in response to the excessive irradiation. The strong absorption of UV light in the range of 260–340 nm exhibited by the emu oil would also contribute to this dermal-protecting property since radiation within this wavelength is known (16, 17) to be associated with connective tissue/cell damage and carcinogenesis.

Accordingly, the present invention in a first aspect consists in a pharmaceutical composition comprising emu oil or a derivative thereof and a compound that acts to provide effective transport across the dermis or mucous membranes.

In a second aspect, the present invention further consists in a method for the treatment or prophylaxis of musculoskeletal and/or dermatological conditions arising from inflammatory reactions of environmental or systemic origins comprising applying to an area so effected by said conditions, an effective amount of a pharmaceutical composition which include emu oil or a derivative or a component thereof and a compound that acts to provide effective transport across the dermis or mucous membranes of said area.

Hereinafter, the term "transport enhancer" will be used to refer to "a compound that acts to provide effective transport across the dermis or mucous membranes". From the foregoing it is evident that there are fundamental differences between the compositions of the present invention and those disclosed and taught in WO 90/07331. These are firstly that contrary to the disclosure of WO 90/07331, the present inventors have found that emu oil deficient in linolenic acid is highly active and secondly, emu oil contains other compound(s) which alone or when combined with a transport enhancer provide an effective anti-inflammatory composition. These compounds are not present in linseed oil.

Preferably, the compositions used consist of 1–99% of emu oil by volume combined with 99–1% of the transport enhancer. More preferably, the composition consists of 4 parts by volume of emu oil with 1 part by volume of the transport enhancer. The transport enhancer can be either methyl, ethyl or isopropyl salicylate either isopropyl, butyl or amyl alcohol; cineole; eucalyptus oil; tea tree oil; oil of wintergreen or other like substances. Cineole, eucalyptus oil, tea tree oil and isopropyl alcohol are preferred.

In a third and more general aspect, the present invention still further consists in a biologically active yellow-coloured component of emu oil prepared by:

fractionating emu oil diluted with hexane using a florisil column;

eluting said column succesively with hexane, dichloromethane and 10% methanol in dichloromethane;

separating a biologically active yellow coloured component from the 10% methanol in dichloromethane fraction;

optionally fractionating said yellow coloured component diluted in hexane using a silica column;

eluting said column succesively with hexane, dichloromethane and 10% methanol in dichloromethane; and separating a biologically active yellow coloured component from the 10% methanol in dichloromethane fraction.

This biologically active yellow-coloured component may be included in topical, oral and systemic compositions for the treatment or prophylaxis of musculoskeletal and/or dermatological conditions arising from inflammatory reactions of environmental or systemic origins.

The Nature of the Active Principal of Emu Oil

As is evident in Table 6, the overall fatty acid composition of the emu oil preparations were not too dissimilar to that of chicken. However, while the chicken oils were colourless, the emu oils were invariably yellow coloured. This suggested that the anti-inflammatory activity of the latter was associated with the yellow colour. Experiments were undertaken to confirm this observation. Firstly, active emu oil was exposed to strong ultraviolet light radiation (as sunlight) for several weeks, a procedure which was observed to lead to a diminution of the intensity of the yellow colour. Such preparations were shown to be inactive when examined for anti-inflammatory activity in the rat polyarthritic model (Table 8). Interestingly, anti-inflammatory activity could be restored to the oil by the addition of retinyl acetate but not $\beta$-carotene (Table 8). The activity of the retinyl acetate was not surprising in view of the numerous publications describing the anti-inflammatory activity of this and related structures (18–22). The anti-inflammatory activity and colour of the emu oils could also be abolished by subjecting them to chemical oxidation for example by mixing with benzoyl peroxide in an organic solvent (Table 8). Further support for the contention that anti-inflammatory activity of the emu oil preparation was dependent on the yellow components is provided by data shown in Table 9. In this experiment UV light-bleached emu oil when admixed with squalene and a denatured M. tuberculosis preparation (the arthritogen used routinely to produce polyarthritis in the rat) produced a similar result to that when olive oil was admixed with the same inflammatory materials. In contrast, when yellow emu oil mixed with squalene and M. tuberculosis was injected subdermally into dark Agouti rats no inflammation, as indicated by swelling of the paws and loss of weight, was observed for up to 18 days post injection. These findings clearly identify the yellow components in emu oil as possessing remarkable prophylactic anti-inflammatory/immuno-regulant activity, apart from their ability to modulate disease once initiated (Tables 1–4, 7, 8).

A chromatographic method was developed for the separation of the yellow components of the emu oil and this is described below. Significantly these purified yellow fractions were found to exhibit extremely potent anti-inflammatory activity. As is shown in Table 10 using olive oil and cineole as a dilutant the emu yellow components YCA and YCB were approximately one tenth the activity of retinyl acetate on a weight basis, but half the activity when inactive UV-light bleach-cineole was used as a vehicle. From this latter finding it could be concluded that the triglycerides or other non-coloured compounds in the emu oil may be acting synergistically with the active principle.

Isolation and Purification of the Emu Oil Yellow Component

Emu oil (Batch 67) was diluted 1:1 with hexane and fractionated on an activated florisil column (1 g of oil per 12 g of florisil). Additional hexane (100 ml per g of oil) was passed through the column followed by dichloromethane (100 ml per g of oil) and 10% methanol in dichloromethane (100 ml per g of oil). The material eluting in the hexane and the dichloromethane fraction (0.89 g) was colourless and the material eluting in the 10% methanol in dichloromethane fraction (0.11 g) was a yellow colour.

The material eluting in the 10% methanol in dichloromethane fraction was diluted 1:1 with hexane and applied to a silica column (1 g of yellow material per 12 g of silica). Additional hexane (100 ml per g of oil) was passed through the column followed by dichloromethane (100 ml per g of oil) and 10% methanol in dichloromethane (100 ml per g of oil).

The material eluting in the hexane and the dichloromethane fraction was colourless (0.64 g) and the material eluting in the 10% methanol in dichloromethane fraction (0.36 g) was a yellow colour. Pure yellow component (YCA/YCB) was separated from the methanol/dichloromethane by evaporation.

The 10% methanol in dichloromethane fraction from the silica column was analysed by gas chromatography using an on-column injection technique. The material was shown to be free of trigylcerides but consisted principally of two closely eluting peaks. These two peaks corresponded to two peaks observed when the unpurified oil was analysed using the same technique.

Hydrolysis with sodium methoxide of the 10% methanol in dichloromethane fraction from the silica column showed that it was composed of saturated and unsaturated fatty acids esterified with a series of compounds as yet unidentified. Indications are that the saturated and unsaturated fatty acids are C16–C18 with some shorter and longer chain length acids present.

The compositions of the invention may be readily formulated by those skilled in the art using appropriate vehicles to produce a variety of topical compositions including liniments, aerosols, creams, ointments, gels, lotions and the like.

MODES FOR CARRYING OUT THE INVENTION

The emu oil, its partially purified active fractions or the active components themselves corresponding to structures (I) may be administered to animals and, man topically, systemically or orally.

For topical administration the use of "transport enhancer" as described herein is generally necessary although the emu oil, its purest fractions or pure substance also show dermal absorption when applied with suitable emulgents such as monostearin, cetomacrogol, cetrimide, sorboline, or cetostearyl alcohol, etc.

For systemic administration by subcutaneous or intramuscular injection the purified active fractions may be used directly. Alternatively the compounds may be admixed with a neutral vehicle such as a vegetable oil, or acacia gum and injected as a dispersed suspension.

For oral administration soft gelatin capsules containing the purified fractions or the active principle dispersed in acacia or vegetable oil are preferred.

Example I

| | |
|---|---|
| Emu Oil | 10% |
| Eucalyptus oil | 2% |
| Menthol | 0.1% |
| Sorboline | 85% |
| Polychol | 2% |
| (trade mark of Croda Chemicals Ltd) | |
| Propylparaben | 0.2% |
| Antioxidant Topanol (trade mark of ICI) | 0.2% |
| Perfumes | 0.5% |

Example II

A cream formulation for topical application:
An injectable preparation for intramuscular administration:

The yellow component (YC) of emu oil prepared by chromatography as described herein was sterilized by filtration through membrane a filter (0.2 micron, Gelman Sciences) directly into sterile amber coloured glass ampoules which were heat sealed under nitrogen. Such preparation would be expected to remain active for several years at 4° C. in the absence of light.

Example III

An oral form of the partially purified yellow component of emu oil was prepared by diluting out the yellow component (YC) with 4 parts of edible vegetable oil, for example canold oil, and encapsulating this mixture into a soft gelatin capsule.

Whilst the present invention has been described with reference to emu oil, it is possible that other animals may well produce fatty material having an equivalent activity.

In addition, it will be appreciated by those skilled in the art that numerous variations and modifications may be made to the present invention without departing from its spirit or scope.

REFERENCES

1. Kroman N., Green A. Epidemiological Studies in Upernavik District, Greenland. Acta. Med. Scand. 208, 401–406, 1980.
2. Kremer J. M. et al Effects of Manipulation on the Dietary Fatty Acids on Clinical Manifestations of Rheumatoid Arthritis. The Lancet. Jan. 26, 184–187, 1985.
3. Kunkel S. L., Fantone J. D., Ward P. A. and Zurier R. B. Modulation of Inflammatory Reactions by Prostaglandins. Prog. Lipid. Res. 2, 633–640, 1981.
4. Fishcher S., Weber P. C. Prostaglandin $I_3$ is Formed In Vivo in Man After Dietary Eicosapentaenoic Acid. Nature. 307, 165–168, 1984.
5. Mead C. J., Mertin J. Fatty Acids and Immunity. Adv. Lipid. Res. 16, 127–165, 1978.
6. Kunkel S. L., Ogawa H., Ward P. A., Zurler R. B. Suppression of Chronic Inflammation by Evening Primrose Oil. Prog. Lipid. Res. 20, 885–888, 1982.
7. Jantti J., Nikkari T., Solakivi T., Vapaatalo H., Isomaki H. Evening Primrose Oil in Rheumatoid Arthritis: Changes in Serum Lipid and Fatty Acids. Annals. Rheum. Dis. 48 124–127, 1989.
8. Hansen M., Lerche A., Kassis V., Lorenzen J., Sondergaard J. Treatment of Rheumatoid Arthritis with Prostaglandin $E_1$, precursors, cis-linolenic acid and alpha-linolenic acid. Scand. J. Rheumatol 12, 85–88, 1983.
9. Hilditch, T. P., and Williams P. N., The chemical constitution of Natural Fats. Chapman and Hall (London) 4th Edition 1964.
10. Whitehouse M. W., Bolt A. G., Ford G. L. and Vernon-Roberts D. Antiarthritic Activity of Polyunsaturated Fatty Acid (PUFA) Derivatives in Adjuvant Arthritis Rats in "Current Problems in Nutrition, Pharmacology and Toxicology"., Eds, McLean A. and Wahlqvist M. L., John Libbey, London, Paris 1988 pp. 101–103.
11. Ashe B. M., Zimmerman N. M. Specific inhibition of human granulocyte elastase by unsaturated fatty acids and activation by the corresponding alcohols. Biochem. Biophys. Res. Commun. 75, 194–199, 1977.
12. Stephens R. W. et. al. A radioassay for proteolytic cleavage of isolated cartilage proteoglycans. Inhibition of human leukocyte elastase and Cathepsin G by anti-inflammatory drugs. Arzneimittel-Forschung 30, 2108–2112, 1980.
13. Starkey P. M. and Barrett A. J. Human lysosomal elastase catalytic and immunological properties. Biochem. J. 155, 265–271, 1976.
14. Malemud C. J. and Janoff A. Human polymorphonuclear leukocyte elastase and Cathepsin G mediate the degradation of lapine articular cartilage proteoglycan. Ann. N.Y. Acad. Sci (USA) 256, 254–262, 1975.
15. Starkey P. M., Barrett A. J. and Burleigh M. C. The degradation of articular collagen by neutrophil proteinase. Biochem. Biophys. Acta. 483, 1977.
16. Freeman R. G., Hudson H. T., Carnes R. Ultraviolet light wavelength factors in solar radiation and skin cancer. Int. J. Dermatol. 9, 232–235, 1970.
17. Kligman L., Akin F. J. and Kligman A. The contribution of UVA and UVB to connective tissue damage in hairless mice. J. Invest. Dermatol. 84, 272–276, 1985.
18. Lesnik R. H., Mezick J. A., Capetola R. and Kligman L. H. Topical all-trans-retinoic acid prevents corticosteroid-induced skin atrophy without abrogating the anti-inflammatory effect. J. American Acad. Dermato. 21, 186–190, 1989.
19. Brinckerhoff C. E. and Harris E. D. Modulation by retinoic acid and corticosteroids of collagenase production by rabbit synovial fibroblasts treated with phorbol myristate acetate or polyethylen glycol. Biochem. Biophys. Acta 677, 424–432, 1981.
20. Chatellard Gruaz D., Didierjean L., Gumowski-Sunek D. and Saurat J. H. Effect of topical retinoic acid on the interleukin 1 alpha and beta immunoreactive pool in normal human epidermis. Brit. J. Derm. 123, 283–289, 1990.
21. Hope W. C., Patel B. J., Fiedler-Nagy C. and Wittreich B. H. Retinoids inhibit phospholipase $A_2$ in human synovial fluid and arachidonic acid release from rat peritoneal macrophage. Inflammation, Vol. 14, No. 5, 1990.
22. Hanglow A. C., Bachmann H., Rosenberger M. and Coffey J. W. Effects of a novel anti-inflammatory retinoid-like 2,4,6,8-nonatetraenoic adjuvant-induced arthritis. Int. J. Immunopharmac. Vol. 12, No. 7, 703–712, 1990.

TABLE 1

Effects of dermally-applied oils - ethyl salicylate (ES) combinations (1:4 v/v) (2 ml/kg) in suppressing paw inflammation (oedema) in male polyarthritic rats (4 per group).

| Combination | Mean Increase in Rear Paws Diameter (mm) | |
|---|---|---|
| | Days 12–16 | Days 16–19 |
| None* (sham rub) | 1.65 | 0.17 |
| Corn oil-ES* | 1.52 | 0.40 |
| Evening primrose-ES* | 0.85 | 0.64 |
| Rape seed-ES* | 1.10 | 0.78 |
| Emu oil (batch 135)-ES | 0.51 | 0.51 |

*Data modified from reference (10)
Rat oedema induced by tail base injection of 500 μg *M. tuberculosis* in 500 μL squalene on day 0. Oil-ES combinations were applied to shaved dorsal skin (16 cm²), once daily on days 12–15 inclusive. Assessments were made on days 12, 16, and 19 inclusive.

TABLE 2

Anti-inflammatory activity of Emu Oil (EO) Formulations And Other Oils Applied Dermally (2 ml/kg) to Male Polyarthritic Rats (4 Per Group)

| Treatment | Days 12–16 [Increase in thickness (mm)] | | | | Days 16–10 ("Rebound") [Increase in thickness (mm)] | | | |
|---|---|---|---|---|---|---|---|---|
| | Rear Paws | Tail | Front Paws | Wt Chge (g) | Rear Paws | Tail | Front Paws | Wt Chge (g) |
| Sham rub (no EO) | 0.99 | 0.35 | 2.4+ | 0 | 0.0 | −0.04 | −0.5+ | +02 |
| Emu Oil Batch 157 (EO 157) | 1.02 | −0.33 | 3.2+ | −04 | 1.04 | 0.17 | 1.3+ | −05 |
| EO 157-methyl salicylate (1:4 v/v) | 0.40 | −0.07 | 1.9+ | −08 | 0.93 | −0.02 | 1.6+ | −06 |
| EO 157-methyl salicylate (9:1 v/v) | 0.12 | −0.07 | 0.3+ | −07 | 0.93 | 0.40 | 2+ | +4 |
| EO 157-ethyl salicylate (9:1 v/v) | 0.13 | −0.32 | 0.5+ | +0.2 | 0.45 | 0.02 | 1.5+ | −01 |
| EO 157 (Propyl) salicylate (9:1 v/v) | −0.14 | −0.08 | −0.1+ | +04 | 0.36 | 0.36 | 1.6+ | +03 |
| EO 157-Propan-2-ol (4:1 v/v) | −1.10 | 0.28 | 0 | +12 | 0.76 | 0.38 | 0.6+ | −01 |
| EO 157-Propan-2-ol (9:1 v/v) | 0.02 | −0.03 | 0.8+ | +04 | 0.36 | 0.09 | 0.8+ | −06 |
| EO 157-Propan-2-ol (19:1 v/v) | 0.01 | −0.08 | 0.5+ | +06 | 0.38 | 0.33 | 0.7+ | +02 |
| EO 157-cineole (1:4 v/v) | 0.17 | −0.24 | 1.6+ | +02 | 0.72 | 0.16 | 0.1+ | −0.3 |
| Canola-methyl salicylate (1:4 v/v) | 0.55 | 0.06 | 2.2+ | +02 | 0.43 | 0.35 | −0.2+ | −02 |
| Corn oil-methyl salicylate (1:4 v/v) | 0.89 | 0.18 | 2.3+ | +05 | 0.05 | −0.13 | −0.7+ | −01 |

Rat oedema induced by tail base injection of 500 μg *M. tuberculosis* in 50 μL squalene on day 0. EO formulations were applied to shaved dorsal skin (16 cm²), once daily on days 12–15. Assessment made on days 12, 16, 10.

TABLE 3

Anti-inflammatory Activity of Emu Oil (EO) Formulations And Other Oils Applied Dermally (2 ml/kg) to Male Polyarthritic Rats (4 Per Group)

| Treatment | Days 12–16 [Mean Thickness (mm)] | | | WT Chge (g) | Days 16–19 [Mean Thickness (mm)] | | | WT Chge (g) |
|---|---|---|---|---|---|---|---|---|
| | Rear Paws | Tail | Front Paws | | Rear Paws | Tail | Front Paws | |
| Sham rub (ethanol propylenglycol, 2:1 v/v) | 0.83 | 0.62 | 2.0 | −09 | 0.10 | −0.01 | −0.4+ | +06 |
| Emu oil batch 181 (EO 181)-Cineole (4:1, v/v) | 0.08 | 0.03 | 0.3+ | −03 | 0.29 | 0.08 | 0.8+ | +11 |
| Johnson's Baby Oil-Cineole (4:1, v/v) | 0.61 | 0.27 | 1.1+ | −02 | 0.06 | 0.03 | 0.4+ | +08 |
| EO 181-Baby Oil-Cineole (2:2:1, v/v) | 0.24 | 0.55 | 1.1+ | −09 | 0.31 | 0.17 | −0.7+ | +04 |
| Chicken Oil-Cineole (4:1, v/v) | 0.77 | 0.08 | 1.2+ | +08 | 0.06 | 0.35 | −0.2+ | +03 |

TABLE 3-continued

Anti-inflammatory Activity of Emu Oil (EO) Formulations And Other Oils Applied Dermally (2 ml/kg) to Male Polyarthritic Rats (4 Per Group)

| Treatment | Days 12-16 [Mean Thickness (mm)] | | | WT Chge (g) | Days 16-19 [Mean Thickness (mm)] | | | WT Chge (g) |
|---|---|---|---|---|---|---|---|---|
| | Rear Paws | Tail | Front Paws | | Rear Paws | Tail | Front Paws | |
| EO 181-Terpineol (4:1, v/v) | 0.21 | 0.62 | 0.9+ | −16 | 0.38 | 0.68 | 0.5+ | +04 |

Rat oedema induced by tail base injection of 500 μg *M. tuberculosis* in 50 μL squalene on day 0. EO formulations were applied to shaved dorsal skin (16 cm$^2$), once daily on days 12-15. Assessment made on days 12, 16, 19.

TABLE 4

Anti-inflammatory Activity of Emu Oil (EO) Formulations and Other Oils Applied Dermally (2 ml/kg) to male Polyarthritic Rats (4 Per Group)

| | Days 12-16 [Mean Thickness (mm)] | | | Wt Chge (g) | Days 16-19 [Mean Thickness (mm)] | | | Wt Chge (g) |
|---|---|---|---|---|---|---|---|---|
| | Rear Paws | Tail | Front Paws | | Rear Paws | Tail | Front Paws | |
| Sham rub (DMSO-glycerol 4:1 v/v) | 0.81 | 0.69 | 1.3+ | −02 | −0.12 | 0.38 | 0 | −07 |
| Emu oil batch 135 (EO 135)-Cineole (4:1, v/v) | 0.31 | 0.26 | 1.1+ | +0.7 | 0.16 | 0.02 | 0.7+ | −01 |
| Emu oil batch 181 (EO 181)-Cineole (4:1, v/v) | 0.20 | 0.16 | 0.9+ | −09 | 0.42 | 0.20 | 0.6+ | −04 |
| *Emu oil fraction 181A-Cineole (4:1 v/v) | 0.25 | −0.27 | 0.3+ | +0.7 | 1.00 | 0.03 | 1.8+ | −03 |
| *Emu oil fraction 181B-Cineole (4:1 v/v) | 1.14 | 0 | 2+ | −12 | 0.31 | 0 | 0.5+ | −03 |
| Olive Oil-Cineole (4:1 v/v) | 1.03 | 0.79 | 1.7+ | −06 | 0.26 | 14 | 0 | −03 |
| Safflower oil-cineole (4:1 v/v) | 0.70 | 0.54 | 0.7+ | +06 | 0.04 | 0.08 | 0.2+ | −06 |
| Emu oil 181A-Eucalyptus oil (4:1 v/v) | 0.35 | 0.34 | 0.7+ | +06 | 0.03 | 0.13 | 0.3+ | +11 |
| Emu oil 181A-Tea Tree oil (4:1 v/v) | 0.47 | 0.25 | 1.5+ | −08 | 0.25 | 0.08 | 1.3+ | +04 |
| Emu oil 181A-Tea Tree oil (9:1 v/v) | 0.29 | −0.20 | 0.3+ | 0 | 0.41 | 0.53 | 1.3+ | +05 |
| Emu oil 181A-Tea Tree oil (19:1 v/v) | 0.08 | 0.11 | 0.5+ | +05 | 0.54 | 0.04 | 1.7+ | +13 |
| Emu oil 181-Amyl acetate (4:1 v/v) | 0.26 | 0.02 | 0.8+ | +06 | 0.74 | 0.30 | 0.8+ | +08 |

*EO 181 subfraction A = filtrate from freezing experiments on Emu Oil batch 181 (EO 181)
*EO 181 subfraction B = retententate from above
*DMSO = Dimethyl sulphoxide
Rat oedema induced by tail base injection of 500 μg *M. tuberculosis* in 50 μL squalene on day 0. EO formulations were applied to shaved dorsal skin (16 cm$^2$), once daily on days 12-15. Assessment made on days 12, 16, 19.

TABLE 5

GLC-Mass Spectral Analysis of Emu Oil and Other Products (as % of Total)

| Identification no. (batch) | 135 | 136 | 137 | 138 | 157 | 158* | 159+ | 181 | 203 | 202 |
|---|---|---|---|---|---|---|---|---|---|---|
| Palmitic (C16:0) | 24.1 | 26.0 | 31.1 | 28.2 | 27.3 | 32.0 | 26.5 | 27.5 | 13.2 | 5.6 |
| Palmitoleic (C16:1) | ND | ND | ND | ND | ND | ND | ND | 4.0 | <1.0 | ND |
| Stearic (C18:0) | 10.7 | 11.6 | 9.0 | 10.5 | 9.8 | 11.3 | 9.2 | 8.4 | 2.7 | 1.4 |
| Oleic (C18:1) | 59.9 | 58.1 | 55.2 | 56.6 | 43.7 | 39.8 | 44.2 | 54.2 | 62.4 | 59.9 |
| Linoleic (C18:2) | 5.3 | 4.3 | 4.7 | 4.7 | 7.4 | 6.8 | 8.1 | 5.9 | 20.1 | 23.8 |
| a-Linolenic (C18:3) | ND | ND | ND | ND | 11.7 | 10.1 | 11.9 | ND | 1.7 | 9.1 |
| g-Linolenic (C18:3) | ND | ND | ND | ND | ND | ND | ND | ND | ND | ND |

\* - Sediment after cooling EO 157 to 10° C.
+ - Supernatant after cooling EO 157 to 10° C.
202 - Canola Brand "polyunsaturated" cooking oil
ND - Not detectable
- A commercial preparation of EO diluted with peanut oil (4:1 v/v)

TABLE 6

Comparison of Fatty Acid Composition of Free Range Chicken and Emu Fats (Data generated after methoxide hydrolysis and GLC expressed as %).

| Fatty Acid | Number Carbons | Unsaturation | Emu | Chicken |
|---|---|---|---|---|
| Myristic | C14 | 0 | 0.32 | 1.25 |

TABLE 6-continued

Comparison of Fatty Acid Composition of Free Range Chicken and Emu Fats (Data generated after methoxide hydrolysis and GLC expressed as %).

| Fatty Acid | Number Carbons | Unsaturation | Emu | Chicken |
|---|---|---|---|---|
| Palmitic | C16 | 0 | 21.27 | 22.03 |
| Palmitoleic | C16 | 1 | 5.57 | 6.85 |
| Stearic | C18 | 0 | 7.81 | 5.94 |
| Oleic | C18 | 1 | 54.52 | 48.37 |
| Linoleic | C18 | 2 | 7.24 | 12.06 |
| Linolenic | C18 | 3 | 0.41 | 0.86 |
| Arachidic | C20 | 0 | 0.37 | 0.51 |
| Arachidonic | C20 | 4 | <0.2 | <0.2 |
| Total polyunsaturated Fatty Acids present | | | 7.65 | 12.92 |

TABLE 7

Summary of Anti-inflammatory Activity expressed as difference between treated and untreated paw swelling of Emu Oil (EO) and other oil formulations with regard to their unsaturated FA content.

| Oil Preparation | % Unsaturated FA Content | | | Transdermal Excipient | | | | | | | |
|---|---|---|---|---|---|---|---|---|---|---|---|
| | Linolenic | Linoleic | Oleic | None | Ethyl Sal. | Methyl Sal. | Iso Propanol | Cineole | Tea Tree Oil O | Terpinol | Eucalyptus Oil | Amyl Acetate |
| Emu oil batch 135 | 0.0 | 5.3 | 59.9 | ND | 1.14 | ND | ND | 0.50 | DN | DN | ND | ND |
| Emu oil batch 157 | 11.7a | 7.4 | 43.7 | −0.03 | ND | 0.59 | 0.66 | 0.82 | ND | ND | ND | ND |
| Emu oil batch 203 | 1.7a | 20.1 | 62.4 | +0.02 | ND | ND | ND | 0.79 | ND | ND | ND | ND |
| Emu oil batch 181 | 0 | 5.9 | 54.2 | ND | ND | ND | ND | 0.75 | 0.36 | 0.62 | ND | 0.79 |
| Emu oil batch 181A | 0 | ND | ND | −0.17 | ND | ND | ND | 0.70 | 0.78 | ND | 0.70 | ND |
| Corn oil* | 0 | 34–62% | 19–49% | ND | 0.13 | 0.10 | ND | ND | ND | ND | ND | ND |
| Evening primrose* | 9.08 gamma | 71.3 | 11.4 | ND | 0.80 | ND | ND | ND | ND | ND | ND | ND |
| Rape seed* | 8.62 alpha | ND | ND | ND− | 0.55 | ND | ND | ND | ND | ND | ND | ND |
| Canola | 9.1 alpha | 23.8 | 59.9 | ND | ND | 0.44 | ND | ND | ND | ND | ND | ND |
| Safflower* | 0.04– | 76.6–79.0 | 13.4 | ND | ND | ND | ND | 0.35 | ND | ND | ND | ND |
| Olive* | 0.7 alpha | 6.3 | 78.1 | ND | ND | ND | ND | 0.02 | ND | ND | ND | ND |

ND = Not Determined
Sal. = Salicylate
FA = Fatty Acid
* = FA taken from reference (9)

TABLE 8

Anit-inflammatory activity of Emu Oil (E.O.) before and after ultraviolet light (uv) exposure or benzoyl peroxide oxidation with and without some potential Antioxidant Additives in Male Polyarthritic Hooded Rats (4 Per Group)

| Treatment | Dose/kg | Mean changes over: | | | | | | | | |
|---|---|---|---|---|---|---|---|---|---|---|
| | | Days 12-16 Thickness (mm) | | | | | Days 16-20 Thickness (mm) | | | |
| | | Rear Paws | Tail | Front Paws | Wt Chge (g) | Skin Irr. | Rear Paws | Tail | Front Paws | Wt Chge (g) |
| None (sham rub) | 0 ml | 0.75 | 0.45 | 1.5+ | −06 | 0 | 0.40 | 0.23 | 0.3+ | −01 |
| E.O. (Batch 67)-Cineole (4:1 v/v) | 2 ml | −0.06 | 0.43 | 0.3+ | 0 | 0 | 0.50 | 0.27 | 0.7+ | +06 |
| uv-light#-Bleached E.O. (Batch 67)-Cineole (4:1 v/v) | 2 ml | 0.63 | 0.35 | 1.4+ | 0 | 0 | 0.10 | −0.06 | 0 | 0 |
| uv-light#-Bleached E.O. (Batch 67)-Cineole (4:1 v/v) plus R.A. | 20 mg | 0.04 | 0.06 | 0.3+ | +05 | 0.6+ | 0.61 | 0.36 | 0.5+ | +0.4* |
| uv-light#-Bleached E.O. (Batch 67)-Cineole (4:1 v/v) plus B-Carotene | 20 mg | 0.61 | −0.36 | 2+ | −09 | 0.5+ | 0.19 | 0.15 | 0.5+ | +0.6* |
| EO (Batch 181)-Cineole (4:1 v/v) | 2.0 ml | 0.14 | 0.43 | 0.6+ | +01 | 0 | 0.91 | 0.73 | 0.4+ | +03 |
| Oxidised* EO (Batch 181)/Cineole (4:1 v/v) | 2.0 ml | 0.57 | 0.53 | 1.5+ | 0 | 0 | −0.6 | 0.40 | 0.5+ | −11 |
| Ethanol-Prop. glycol (E-Pg) | 2.5 ml | 0.96 | 0.35 | 1.3+ | +03 | 0 | −0.20 | 0.27 | 0.5+ | +06 |
| R.A. in E-Pg | 20 mg | 0.16 | −0.12 | 0.5+ | −02 | 0.6+ | 0.30 | −0.10 | 0.4+ | +10 |

TABLE 8-continued

Anit-inflammatory activity of Emu Oil (E.O.) before and after ultraviolet light (uv) exposure or benzoyl peroxide oxidation with and without some potential Antioxidant Additives in Male Polyarthritic Hooded Rats (4 Per Group)

| | | Mean changes over: | | | | | | | | |
|---|---|---|---|---|---|---|---|---|---|---|
| | | Days 12–16 Thickness (mm) | | | | | Days 16–20 Thickness (mm) | | | |
| Treatment | Dose/ kg | Rear Paws | Tail | Front Paws | Wt Chge (g) | Skin Irr. | Rear Paws | Tail | Front Paws | Wt Chge (g) |
| Trolox-DE in E-Pg | 25 mg | 0.84 | 0.21 | 1.5+ | +04 | 0 | 0.49 | −0.17 | 0.7+ | 0 |

RA = Retinyl acetate; DE = Diethylamine; Trolox = Vit. E analogue;
Rat oedema induced by tail base injection of 500 μg M. tuberculosis in 50 μL squalene on day 0. EO formulations were applied to shaved dorsal skin (16 cm$^2$) daily on days 12–15.
Assessment made on days 12, 16, 19.
uv-light bleaching was achieved by exposign Emu oil in airtight glass container to intense direct sunlight for seven weeks at ambient temperature.
*a sample of Emu oil (1.0 gram) dissolved in 10 ml chloroform was shaken with benzoyl peroxide (100 mg) in 10 ml chloroform at 20° for 16 hours. The chloroform mixture was extracted with H2O (10 ml), organic layer separated, dried and the chloroform removed by rotary evaporation under reduced pressure. The residual oil was used without further treatment for the rat in these experiments as shown above.

TABLE 9

Influence of co-administration* of various oil preparations on the induction of polyarthritis in Dark Agouti rats (three animals per group) using M. tuberculosis in squalene as arthritogen.

| Oil Preparation | Sex | Arthritic Score | Day | ΔWeight | Incidence |
|---|---|---|---|---|---|
| Olive Oil | M | 3.0+ | 14 | +0.07 | 3/3 |
| | F | 3.7+ | 18 | −13 | 3/3 |
| uv-light bleached EO (Batch 67) | M | 3.5+ | 14 | +0.3 | 3/3 |
| | F | 2.9+ | 18 | −0.03 | 2/3 |
| EO (Batch 67)- yellow | M | 0 | 14 | +20 | 0/3 |
| | F | 0 | 18 | +20 | 0/3 |

EO = Emu Oil
*subdermal injection into base of tail day zero

TABLE 10

Anti-inflammatory activity of yellow component (YC) isolated by chromatography from Emu Oil (EO) (see text) using uv-light bleached EO (see Table 7) or olive oil as dilutents. Cineole was used in all experiments as the transdermal excipient (enhancer) at 20% v/v (4:1). (3 Animals were used in each group.)

| | | Mean changes over: | | | | | | | |
|---|---|---|---|---|---|---|---|---|---|
| | | Days 10–14 Thickness (mm) | | | | Days 14–17 | | | |
| Group | Treatment (2.0 ml/kg) | Rear Paws | Tail | Front Paws | Wt Chge (g) | Rear Paws | Tail | Front Paws | Wt Chge (g) |
| A | None | 1.22 | 0 | 4.0+ | −20 | 0.07 | 0.02 | 1.7+ | −07 |
| B | Olive oil-cineole (4:1) | 1.39 | 0.05 | 2.4+ | −31 | 0.29 | 0.33 | 0.3+ | −06 |
| C | (YCA + Olive oil)-cineole (4:1) | 0.39 | −0.15 | 2.6+ | −27 | 1.43 | 0.09 | 2.7+ | −10 |
| D | (RA + Olive oil)-cineole (4:1) | 0.58 | 0.33 | 2.0 | −16 | 0.32 | 0.53 | 1.5+ | −09 |
| E | uv light bleached EO-cineole (4:1) | 1.45 | 0.14 | 3.0+ | −24 | 0.54 | 0.28 | 0.3+ | −05 |
| F | (YCB + uv light bleached EO)-cineole (4:1) | 0.88 | −0.26 | 2.6+ | −29 | 1.77 | 0.36 | 1.7+ | −10 |
| G | (YCA + uv light bleached EO)-cineole (4:1) | 0.40 | −0.12 | 1.8+ | −15 | 1.50 | 0.42 | 2.8+ | −21 |
| H | (uv light bleached EO RA)-cineole (4:1) | 0.80 | 0.03 | 1.6+ | −24 | 1.53 | 0.20 | 3.0+ | −08 |
| I | EO-cineole (4:1) | 0.46 | 0.07 | 2.2+ | −14 | 1.58 | 0.43 | 2.3+ | −11 |
| J | Olive oil-Farnesol-cineole (3:1:1 v/v) | 1.47 | 0.22 | 1.5+ | −17 | 0.82 | 0.65 | 0.7+ | −06 |
| K | Squalene/Cineole (4:1) | 1.12 | 0.07 | 4.5+ | −19 | 0.38 | 0.10 | 0.5+ | −17 |

YCA = yellow component from EO at 129 mg/kg
YCB - yellow component from EO at 43 mg/kg
RA = Retinol acetate at 10 mg/kg
Squalene = a polyunsaturated hydrocarbon at 1.6 ml/kg
Farnesol = a Triene-ol analogue of Retinol at 0.4 ml/kg

We claim:

1. A biologically active yellow-coloured component of emu oil prepared by:

fractionating emu oil diluted with hexane using a florisil column;

eluting said column successively with hexane, dichloromethane and 10% methanol in dichloromethane; and separating a biologically active yellow coloured component from the 10% methanol in dichloromethane fraction.

2. An anti-inflammatory pharmaceutical composition comprising a biologically active yellow component as claimed in claim 1 and a pharmaceutically acceptable carrier.

3. A composition as in claim 2 in the form of an injectable composition.

4. A composition as in claim 2 in the form of an oral composition.

5. A composition as in claim 2 in the form of a topical composition.

6. The component of claim 1, wherein the preparation of the component further comprises the steps of fractionating said yellow coloured component diluted in hexane using a silica column,
   eluting said column successively with hexane, dichloromethane and 10% methanol in dichloromethane, and
   separating a biologically active yellow coloured component from the 10% methanol in dichloromethane fraction.

7. An anti-inflammatory topical pharmaceutical composition comprising:
   a) an anti-inflammatory selected from the group consisting of emu oil, a yellow-coloured biologically active component isolated from emu oil, and derivatives thereof,
   b) 1 to 99% by volume of one or more compounds that act to provide effective transport of the anti-inflammatory across the dermis or mucous membranes and
   c) a pharmaceutically acceptable carrier.

8. A composition as in claim 7 wherein said one or more compounds that act to provide effective transport are selected from the group consisting of methyl, ethyl or isopropyl salicylate; isopropyl, butyl or amyl alcohol; cineole; eucalyptus oil; tea tree oil and oil of wintergreen.

9. A composition as in claim 8 wherein said one or more compounds that act to provide effective transport are selected from the group consisting of cineole, eucalyptus oil, tea tree oil and isopropyl alcohol.

10. A composition as in claim 7 wherein the emu oil is in a concentration of from 20 to 95% by volume and said one or more compounds that act to provide effective transport are in a concentration of from 5 to 80% by volume.

11. A composition as in claim 10 wherein the emu oil is in a concentration of from 80 to 90% by volume and said one or more compounds that act to provide effective transport are in a concentration of from 10 to 20% by volume.

12. An anti-inflammatory topical pharmaceutical composition comprising 1 to 99% by volume of a biologically active yellow coloured component of emu oil prepared by:
   fractionating emu oil diluted with hexane using a florisil column;
   eluting said column successively with hexane, dichloromethane and 10% methanol in dichloromethane;
   separating a biologically active yellow coloured component from the 10% methanol in dichloromethane fraction, and
   combining the component with 99 to 1% by volume of one or more compounds that act to provide effective transport of said component across the dermis or mucous membranes and a pharmaceutically acceptable carrier.

13. The anti-inflammatory topical pharmaceutical composition as in claim 12 wherein following separation of the biologically active yellow-coloured component from the 10% methanol in dichloromethane fraction, said component is diluted in hexane and fractionated using a silica column.

14. A method for the treatment of musculoskeletal or dermatological conditions arising from inflammatory reactions of environmental or systemic origins comprising administering a component as claimed in claim 1 to a patient in need thereof.

15. A method for the treatment of musculoskeletal or dermatological conditions arising from inflammatory reactions of environmental or systemic origins comprising administering a component as claimed in claim 2 to a patient in need thereof.

16. A method for the prophylaxis of musculoskeletal or dermatological conditions arising from inflammatory reactions of environmental or systemic origins comprising administering a component as claimed in claim 1 to a patient in need thereof.

17. A method for the prophylaxis of musculoskeletal or dermatological conditions arising from inflammatory reactions of environmental or systemic origins comprising administering a component as claimed in claim 2 to a patient in need thereof.

* * * * *